United States Patent [19]

De Nijs

[11] Patent Number: 5,150,718

[45] Date of Patent: Sep. 29, 1992

[54] METHOD OF CONTRACEPTION

[75] Inventor: Hendrik De Nijs, Oss, Netherlands

[73] Assignee: Akzo N.V., Arnhem, Netherlands

[21] Appl. No.: 836,632

[22] Filed: Feb. 14, 1992

Related U.S. Application Data

[60] Continuation of Ser. No. 541,559, Jun. 21, 1990, Pat. No. 5,088,505, Division of Ser. No. 229,066, Aug. 5, 1988, Pat. No. 4,957,119.

[51] Int. Cl.$^5$ .............................................. A61K 9/22
[52] U.S. Cl. ................................. 128/832; 128/833; 128/898; 604/49; 604/890.1
[58] Field of Search ............. 604/49, 890.1, 891.1, 604/892.1; 128/830, 832, 833, 839, 898; 424/457, 465, 486

[56] References Cited

U.S. PATENT DOCUMENTS

| | | | |
|---|---|---|---|
| 3,903,880 | 9/1975 | Higuchi et al. | 128/833 |
| 4,582,052 | 4/1986 | Dunn et al. | 128/839 |
| 4,596,576 | 6/1986 | De Nijs | 128/832 |
| 4,673,565 | 6/1987 | Di Luccio et al. | 424/443 |
| 4,720,384 | 1/1988 | Di Luccio et al. | 424/78 |

OTHER PUBLICATIONS

D. N. Robertson et al., "Release Rates of Levonorgestrel from Silastic Capsules, Homogeneous Rods and Covered Rods in Humans," Chemical Abstracts, 99(8), pp. 308-309, 1983.

D. N. Robertson et al., "Release Rates of Levonorgestrel from Silastic Capsule Homogeneous Rods and Covered Rods in Humans," Contraception, 27(5), 483-495, 1983.

W. Losert et al., "Progestogens with Antimineralocorticoid Activity," Arzneim.-Forsch/Drug. Res. 35(I), No. 2 (1985).

M. J. D. Eenink et al., "Biodegradable Hollow Fibres for the controlled Release of Hormones," J. of Controlled Release 6, pp. 225-247 (1987).

Primary Examiner—Stephen C. Pellegrino
Assistant Examiner—Michael Rafa
Attorney, Agent, or Firm—Donna Bobrowicz; William M. Blackstone

[57] ABSTRACT

The invention relates to an implant of polymeric material which can release a contraceptive agent for a relatively long time when fitted subcutaneously or locally.

8 Claims, No Drawings

METHOD OF CONTRACEPTION

This is a continuation of U.S. Ser. No. 07/541,559, filed Jun. 21, 1990, now U.S. Pat. No. 5,088,505 which was a divisional of U.S. Ser. No. 07/229,066, now U.S. Pat. No. 4,957,119, filed Aug. 5, 1988.

The invention relates to an implant of polymeric material which can release a contraceptive agent for a relatively long time when fitted subcutaneously or locally. More specifically, the invention relates to an implant of such small dimensions that it can be fitted subcutaneously with an ordinary hypodermic needle.

There is a large demand for the development of new, long-acting contraceptives which require a minimum of medical guidance. This is valid in particular for those areas of the world where the medical infrastructure is poor, and where family planning can be organized only to an insufficient extent.

An implant of this type, which can release a contraceptive agent in virtually constant quantities over a period of at least 2 years, but preferably for about 4 to 5 years, is a new development which can certainly supply what is needed. The great problem, however, is that the often large amount of the contraceptive agent with which the polymeric material of the implant has to be charged to guarantee release for about 4 years leads to very large implants which can only be fitted surgically, or to several smaller implants which have to be fitted simultaneously.

The need for subcutaneous fitting of a plurality of (smaller) implants also offers little attraction at the present time.

In theory any polymeric material is suitable for the development of an implant provided only that it is biologically compatible, and also any material with a progestational action. In this context reference may be made, for example, to U.S. Pat. No. 3,279,996 (Long et al.) in which an implant is described which contains an active substance encased by a polysiloxane membrane, and to Dutch Patent 167,850 (Zaffaroni) in which an implant is described in which the active substance is contained in a polymer, and this polymer loaded with active substance is encased by a polymer membrane which completely controls the rate of release. However, if a limit is set to the dimensions of the implant, if a certain amount of implant rigidity is required to facilitate introduction, and, furthermore, if the achievement of a release duration of the contraceptive substance of a minimum of 2 years, and preferably of up to 4 to 5 years, is desired, then all available theoretical solutions seem to fail.

The implant of the invention can be considered one of the release systems known per se which consist of a core of active material encased by a release rate-regulating membrane. The choice of polymers to be used, the choice of the contraceptive substances, and the dimensions of the implant are, however, matched in such a way that a unique release system is obtained which complies completely with the requirements stipulated above.

The implant of the invention is cylindrical or virtually cylindrical with a maximum section of about 2 mm, but preferably between 1.5 and 2.0 mm, and possesses a variable length. The length of the implant will, however, not exceed about 5 cm for practical reasons. The length is preferably between 1 and 4 cm. These dimensions of the implant of the invention are so small that subcutaneous fitting can be carried out with an ordinary hypodermic needle.

The implant of the invention is characterized by:
a) core material of ethylene/vinyl acetate copolymer (hereafter called EVA) having such a molecular weight that the melt index is higher than 10 gram per 10 minutes, and a vinyl acetate content of 20% by weight or more; which core material functions as a matrix for 3-keto-desogestrel, levonorgestrel or gestodene as active contraceptive substances, in a quantity which is sufficient for a long-lasting constant release of at least 15–30 μg of active substance per day, and
b) a membrane having a layer thickness of 50–250 μm which encases the core material and also consists of EVA material, but with such a molecular weight that the melt index is less than 10 gram per 10 minutes, and an acetate content of less than 20% by weight, this implant being completely or virtually completely cylindrical with a maximum external diameter of about 2 mm and a length which is smaller than about 5 cm.

The contraceptively active substance, which can be employed in the context of the present invention, is a highly active progestagen, particularly 3-ketodesogestrel, levonorgestrel or gestodene. These contraceptive substances are highly active substances which show already an effective progestational action with a daily dosage of about 15–30 μg.

This core material can be charged to about 75 percent by weight with the active substance without seriously affecting the utility of the EVA core material. However, a degree of charging of about 50–60% by weight is preferred.

The core material used in the present invention is an EVA polymer with a melt index higher than 10 gram/10 min. and preferably between 25 and 30 g/10 min. The vinyl acetate content of the core material is higher than 20% by weight and preferably higher than 25% by weight.

Very suitable EVA polymers which can be used as core material are, for example, Evatane® with the designations 28-150, 28-399, and 28-400, supplied by ICI and 28.420 and in particular 28.25 and 33.25 supplied by Atochem, and Elvax® with the designations 310, 250, 230, 220, and 210, supplied by Du Pont de Nemours.

The membrane polymer is also an EVA polymer which, however, has a higher molecular weight than that of the core material. The melt index of this membrane material is less than 10 g/10 min., and preferably less than or equal to 8 g/10 min.; the vinyl acetate content is less than 20% by weight.

Suitable EVA polymers which can be used as a membrane are, for example, Evatane® with the designations 501/502 (melt index 2, vinyl acetate content 7.5%), 554/555 (4, 12.5%), 540 (10, 18%) and particularly 571 (8, 15%), Elvax® with the designations 450, 460, 470, 550, 560, 650, 660, 670, 750, 760 and 770, and Evatane® 1080 VN 5 and in particular 1040 VN 4 supplied by Atochem.

The release characteristic of the contraceptive substance (through the membrane) is determined to a large extent by the vinyl acetate content of the EVA membrane.

The implant of the invention is obtained by means of a so-called co-axial extrusion process, a method in which the two EVA polymers are extruded co-axially in preset layer thicknesses with the aid of a co-axial extrusion head.

This co-axial extrusion process means that both polymers are transported in the molten state through the co-axial extrusion head, the molten core material at the same time containing the active substance.

Due to this co-axial extrusion process a contact layer is produced on the interface of the two polymers, which layer is probably fully or partially responsible for the outstanding drug-release properties of the co-extrudate, but in any event prevents the two polymer layers working loose from each other after a period of time, due to disappearance of the active substance from the core polymer, which loosening would fundamentally disturb the release pattern.

The co-axial extrusion process is art known per se so that it will not be gone into further within the scope of this description.

A thick, co-axial filament with a maximum external diameter of about 2 mm, and preferably between about 1,5 and 2.0 mm, is obtained by means of the co-axial extrusion process. The filament is then cut into pieces up to a maximum of about 5 cm long, using conventional techniques.

Although certainly not necessary the circular ends of the implant may—if desired—be additionally protected by an inert polymer, for example polyethylene, polypropylene or the EVA polymer which is used for the membrane, or also, for example, by a (medical grade) silicone adhesive. This protective layer is obtained, for example, by dipping the surface into a smelt or solution of the particular polymer. If necessary, the end can also be singed or pinched closed.

An other embodiment of the implant of the invention possesses a thin layer of polysiloxane around the whole external surface of the implant described above, in addition to the assembly as described above. This polysiloxane is chosen so that the release pattern is not influenced to any appreciable extent; the formation of a second release-rate-regulating layer is thus not intended by this. The layer in question can therefore be extremely thin, even of the order of about 20–50 μm; a somewhat thicker layer, however, is just as permissible.

This protective layer can be obtained by dipping or immersing the implant in a thin tubing of polysiloxane.

The implant of the invention should in each case contain a sufficient quantity of active substance when used for application in humans which is such that it can bring about virtually constant release of the active substance for a minimum of 1 year, which roughly means that the core material must be charged with 5 to 15 mg of 3-keto-desogestrel, levonorgestrel or gestodene. An additional quantity of active substance of about 5 to 15 mg is necessary for each additional year in which the implant must release, so that a quantity of 25–75 mg of active material can be needed for a release duration of 5 years.

The implant of the invention is preferably be used as a subcutaneous implant, but may also be applied locally, e.g. in the uterine or cervical region.

EXAMPLE 1

The active substance 3-keto-desogestrel and EVA core material (melt index 400 g/10 min., vinyl acetate content 28% by weight)-Evatane ® 28-400—were mixed in a ratio of 1:1 (on a weight basis) on a heatable mill at a temperature of 80° C. The polymer sheets charged with 3-keto-desogestrel were reduced in size and then processed into pellets by means of an extruder and a so-called chopper.

The pellets charged with 3-keto-desogestrel intended for the core, and EVA pellets intended for the membrane (melt index 8 g/10 minutes; vinyl acetate content 15% by weight, Evatane ® 571), were transferred to two separate hoppers of the co-axial extrusion apparatus. The co-axial filament as extruded at a temperature of about 100° C. A co-axial filament with an external diameter of 1.9 mm and a skin thickness of 150 μm was obtained with a correct choice and a correct adjustment of the spinneret geometry, the feed rates of the core and skin material to the spinneret, and the winding rate of the fibre. The extruded co-axial filament was cooled in a water bath, and then wound onto bobbins with a draw rate of 0.25 N. The extrusion rate of the filament was 2.3 metres per sec. Typical preparation conditions:

|  | Temperature (°C.) | Pressure (bar) |
| --- | --- | --- |
| Extruder (barrel) | 100 | 60 → 173 |
| Extruder (core) | 80 | 5 → 46 |
| Spinneret | 100 | |

The extruded co-axial filament was then cut into the required length. The filament pieces were wrapped in polysiloxane if desired using polysiloxane tubing (dimensions 1.57/2.41 mm internal/external diameter) to be swelled in cyclohexane and thereafter to be filled with the co-axial filament of the required length, and finally dried under vacuum. The two ends of the implant obtained were sealed with silicone adhesive (medical grade). The external diameter of the implant provided with a polysiloxane layer was 2.5 mm, the external diameter of the implant not provided with a polysiloxane layer was 1.9 mm.

The in vitro release of 3-keto-desogestrel from this implant was tested in 250 ml demineralized water at 37° C. This medium was contained in a 300 ml conical flask which was shaken at 150 cyles/minute with an amplitude of 2.5 cm.

TABLE 1

| Results | | |
| --- | --- | --- |
| In vitro release of 3-keto-desogestrel from a 3 cm implant with and without a polysiloxane external layer. | | |
| | Release (μg/day · cm) | |
| Day | without polysiloxane layer | with polysiloxane layer |
| 1 | 10.0 | 6.7 |
| 2 | 10.7 | 9.7 |
| 3 | 11.3 | 10.0 |
| 4 | 10.3 | 9.7 |
| 7 | 10.3 | 9.3 |
| 9 | 10.0 | 9.7 |
| 10 | 10.0 | 9.7 |
| 14 | 10.3 | 9.7 |

The polysiloxane external layer here has practically no influence on the released pattern.

TABLE 2

| In vitro release of 3-keto-desogestrel from an implant (3 cm) prepared in this way and provided with a polysiloxane layer. The implant was sterilized by heat treatment 20 min, 120° C.). | |
| --- | --- |
| Day | Release (μg/day · cm) |
| 2 | 57.0* |
| 5 | 14.7 |
| 10 | 10.3 |

TABLE 2-continued

In vitro release of 3-keto-desogestrel from an implant (3 cm) prepared in this way and provided with a polysiloxane layer. The implant was sterilized by heat treatment 20 min. 120° C.).

| Day | Release (μg/day · cm) |
|---|---|
| 20 | 11.3 |
| 30 | 10.3 |
| 40 | 10.0 |
| 50 | 10.0 |
| 90 | 9.0 |
| 100 | 9.3 |
| 200 | 8.7 |
| 300 | 8.3 |
| 376 | 8.3 |
| 400 | 7.7 |
| 471 | 7.7 |
| 500 | 8.0 |
| 550 | 7.7 |
| 600 | 8.0 |
| 650 | 7.0 |
| 700 | 6.3 |
| 750 | 6.0 |
| 800 | 6.3 |

*boost of 3-keto-desogestrel because of heat sterilization.

TABLE 3

In vivo release:
Average plasma concentrations (3 dogs) of 3-keto-desogestrel after subcutaneous introduction of an implant prepared in this way (see implant of table 2).

| Day | Plasma concentration (pmol/ml) |
|---|---|
| 1 | 2.11* |
| 2 | 0.81 |
| 3 | 0.62 |
| 7 | 0.66 |
| 14 | 0.46 |
| 21 | 0.53 |
| 28 | 0.49 |
| 35 | 0.56 |
| 42 | 0.56 |
| 51 | 0.56 |
| 56 | 0.54 |
| 63 | 0.59 |
| 70 | 0.60 |
| 77 | 0.59 |
| 84 | 0.59 |
| 91 | 0.63 |

*boost of 3-keto-desogestrel because of heat sterilization.

EXAMPLE 2

The active substance 3-keto-desogestrel and Evatane ® 28-400 were blended in 1:1 weight ratio in a 10 mm extruder at a temperature of 100° C.

The extrudate obtained was granulated with the acid of a pelletizer, after which the pellets were heated in vacuo at 135° C. for one hour.

In the same manner as described in Example 1 a co-axial filament was extruded using the above 3-keto-desogestrel charged pellets as core material and uncharged Evatane ® 571 pellets as membrane material. The membrane thickness of the co-axial fibre was 135 μm, and the external diameter of the implant was 1.65 mm. The dimensions of the polysiloxane tubing were: 1.47 (internal) × 1.95 mm (external diameter). The ends of the 4-cm long implant were sealed with medical grade silicone adhesive. The external diameter of an implant provided with a polysiloxane layer was 2.05 mm.

Typical preparation conditions of the relevant co-axial filament:

| | Temperature (°C.) | Pressure (bar) |
|---|---|---|
| Extruder (barrel) | 80 → 100 | 50 → 160 |
| Extruder (core) | 70 → 85 | 60 → 70 |
| Spinneret | 100 | |

TABLE 4

In vitro release of 3-keto-desogestrel from this 4 cm long implant. The implant was gamma-sterilized (25 kGy).

| Day | Release (μg/day · cm) |
|---|---|
| 1 | 10.0* |
| 2 | 7.8 |
| 3 | 7.8 |
| 4 | 7.5 |
| 10 | 8.0 |
| 20 | 7.8 |
| 30 | 7.3 |
| 40 | 7.3 |
| 50 | 7.3 |
| 100 | 6.0 |
| 150 | 6.5 |
| 200 | 6.0 |
| 250 | 5.5 |
| 300 | 5.8 |
| 350 | 5.3 |
| 400 | 5.0 |
| 450 | 4.6 |
| 500 | 4.3 |
| 550 | 4.0 |

*boost of 3-keto-desogestrel is minimal as gamma sterilization was used instead of heat sterilization.

EXAMPLE 3

Analogous to Example 2, a co-axial filament was spun, but in this case with a membrane thickness of 90 μm. The external diameter of the implant was also about 1.65 mm in this case. Polysiloxane tubing (1.47 × 1.95 mm) was again used for the polysiloxane jacket and the ends were sealed with medical-grade silicone adhesive. The external diameter of the implant provided with a polysiloxane layer was 2.05 mm.

Typical preparation condition of the co-axial filament.

| | Temperature (°C.) | Pressure (bar) |
|---|---|---|
| Extruder (barrel) | 75 → 100 | 160 → 150 |
| Extruder (core) | 60 → 100 | 150 → 110 |
| Spinneret | 125 | |

The length of the implant was 3 cm.

TABLE 5

In vitro release of 3-keto-desogestrel from this non-sterilized implant:

| Day | Release (μg/day · cm) |
|---|---|
| 1 | 13.7 |
| 6 | 9.7 |
| 9 | 9.7 |
| 10 | 10.7 |
| 20 | 10.7 |
| 30 | 9.3 |
| 40 | 9.0 |
| 50 | 8.7 |
| 60 | 9.7 |
| 70 | 9.3 |
| 80 | 9.0 |
| 90 | 9.3 |
| 100 | 8.3 |

TABLE 5-continued

| In vitro release of 3-keto-desogestrel from this non-sterilized implant: | |
|---|---|
| Day | Release (μg/day · cm) |
| 110 | 9.0 |

EXAMPLE 4

Co-axial filament was obtained according to the method described in Example 2.

The filament consists of Evatane® 28.25 as core material and Evatane® 1040 VN 4 as the membrane material.

Further data:
- membrane thickness: 75 μm;
- core material charged with 60% (wt) 3-keto-desogesterel;
- external diameter of the implant: 1.7 mm;
- length implant: 3,0 cm;
- polysiloxane jacket up to external diameter: 2,05 mm;
- sealing of the implant ends with silicone adhesive.

TABLE 6

| In vitro release from the non sterilised implant: | |
|---|---|
| Day | Release (μg/day · cm) |
| 1 | 24.7 |
| 5 | 22.0 |
| 10 | 13.7 |
| 20 | 12.8 |
| 30 | 12.3 |
| 40 | 11.0 |
| 50 | 11.3 |
| 60 | 11.3 |
| 70 | 11.0 |
| 80 | 11.0 |
| 90 | 10.7 |
| 100 | 10.3 |
| 110 | 10.3 |
| 120 | 8.3 |
| 130 | 10.0 |
| 140 | 8.7 |
| 150 | 8.3 |
| 160 | 9.3 |

EXAMPLE 5

Same procedure and material as described in Example 4.

Specifications:
- core material: Evatane® 28.25;
- membrane: Evatane® 1040 VN 4
- membrane thickness: 60 μm
- core charged with 60% (wt) 3-keto desogestrel;
- externel diameter: 2,0 mm;
- length: 4,0 cm;
- no polysiloxane jacket;
- no sealing of implant ends.

TABLE 7

| In vitro release: | |
|---|---|
| Day | Release (μg/day · cm) |
| 1 | 43.9 |
| 5 | 27.8 |
| 10 | 24.9 |
| 20 | 21.3 |
| 30 | 21.1 |
| 40 | 18.9 |
| 50 | 19.1 |
| 60 | 17.4 |
| 70 | 15.4 |
| 80 | 16.1 |
| 90 | 18.5 |
| 100 | 16.8 |
| 110 | 16.5 |
| 120 | 16.3 |

I claim:

1. A method of contraception comprising: subcutaneously or locally administering an implant said implant comprising:
   core material of ethylene/vinyl acetate copolymer having such a molecular weight that the melt index is equal to or greater than 10 grams/10 minutes, and a vinyl acetate content of at least 20% by weight, which core material functions as a matrix for at least one highly active progestogen present in a quantity sufficient for a release rate of greater than 30 μg of said progestogen per day over a term of at least one year, and
   a membrane having a layer thickness of 50-250 μm which encases the core material and also consists of ethylene/vinyl acetate copolymer, but with such a molecular weight that the melt index is less than or equal to 10 grams/10 minutes, and a vinyl acetate content of less than 20% by weight, which membrane, with the core material, forms a contact layer at the interface of the core material and membrane thus preventing the core material and membrane, from separating from one another.

2. The method of claim 1, wherein the core material of said implant comprises an ethylene/vinyl acetate copolymer with a melt index between 25 and 30 grams/10 minutes and a vinyl acetate content of greater than 25% by weight.

3. The method of claim 1, wherein the membrane of said implant comprises an ethylene/vinyl acetate copolymer with a melt index less than or equal to 8 grams/10 minutes and a vinyl acetate content of less than 20% by weight.

4. The method of claim 1, wherein the highly active progestogen comprises 3-ketodesogestrel.

5. The method according to claim 1, wherein said implant is of essentially cylindrical shape with a maximum external diameter of about 2 mm and a length of less than about 5 cm.

6. The method of claim 1, wherein said core of the implant comprises about 50 to 75% contraceptive substance and from about 50 to 25% ethylene vinyl acetate copolymer.

7. The method of claim 6, wherein the ends of the implant are covered by an inert polymer.

8. The method of claim 3, wherein the implant further comprises a layer of polysiloxane coating the entire implant.

* * * * *